(12) United States Patent
Thompson et al.

(10) Patent No.: US 9,333,284 B2
(45) Date of Patent: May 10, 2016

(54) HEART ASSIST DEVICE

(71) Applicant: Cardio Assist Ltd., London (GB)

(72) Inventors: Raymond Thompson, Kent (GB); Magdi Habib Yacoub, London (GB)

(73) Assignee: Heart Biotech Limited, London (GB)

( * ) Notice: Subject to any disclaimer, the term of this patent is extended or adjusted under 35 U.S.C. 154(b) by 0 days.

(21) Appl. No.: 13/856,809

(22) Filed: Apr. 4, 2013

(65) Prior Publication Data

US 2013/0289335 A1   Oct. 31, 2013

Related U.S. Application Data

(63) Continuation of application No. 12/934,300, filed as application No. PCT/GB2008/050217 on Mar. 26, 2008, now abandoned.

(51) Int. Cl.
*A61M 1/10*    (2006.01)
*A61M 1/12*    (2006.01)

(52) U.S. Cl.
CPC ............. *A61M 1/1037* (2013.01); *A61M 1/107* (2013.01); *A61M 1/1053* (2013.01); *A61M 1/122* (2014.02); *A61M 1/1043* (2014.02); *A61M 1/1086* (2013.01)

(58) Field of Classification Search
CPC ... A61M 1/10; A61M 1/1037; A61M 1/1043; A61M 1/1053; A61M 1/107; A61M 1/122

USPC ..................... 600/16, 17; 604/65, 66, 67, 503
See application file for complete search history.

(56) References Cited

U.S. PATENT DOCUMENTS

| | | | | |
|---|---|---|---|---|
| 3,553,736 A * | 1/1971 | Kantrowitz et al. | ......... | 623/3.21 |
| 4,195,623 A * | 4/1980 | Zeff et al. | ........ | 600/18 |
| 4,222,127 A * | 9/1980 | Donachy et al. | ............ | 623/3.21 |
| 4,756,302 A * | 7/1988 | Portner et al. | ................ | 600/17 |
| 4,904,255 A * | 2/1990 | Chareire et al. | ............ | 623/3.22 |
| 4,938,766 A * | 7/1990 | Jarvik | ........... | 623/3.17 |
| 5,443,504 A * | 8/1995 | Hill | ............. | 623/3.12 |
| 5,653,676 A * | 8/1997 | Buck et al. | ........ | 600/16 |
| 5,722,930 A * | 3/1998 | Larson et al. | ................ | 600/16 |
| 5,980,448 A * | 11/1999 | Heilman et al. | ................ | 600/16 |
| 6,066,085 A * | 5/2000 | Heilman et al. | ................ | 600/16 |
| 6,808,484 B1 * | 10/2004 | Peters et al. | ........ | 600/18 |
| 7,588,530 B2 * | 9/2009 | Heilman et al. | ................ | 600/16 |
| 2002/0072698 A1 * | 6/2002 | Chiang et al. | ................ | 604/6.11 |
| 2004/0054251 A1 * | 3/2004 | Liotta | .............. | 600/17 |
| 2004/0068224 A1 * | 4/2004 | Couvillon et al. | ............. | 604/67 |
| 2006/0287568 A1 * | 12/2006 | Jassawalla et al. | ............. | 600/16 |
| 2007/0112325 A1 * | 5/2007 | Wieselthaler | ................ | 604/500 |
| 2008/0045777 A1 * | 2/2008 | Jassawalla et al. | ............. | 600/16 |
| 2011/0071337 A1 * | 3/2011 | Thompson et al. | ............ | 600/16 |

* cited by examiner

*Primary Examiner* — Christopher A Flory
(74) *Attorney, Agent, or Firm* — Saul Ewing LLP

(57) ABSTRACT

A ventricular assist device comprising a housing defining an interior space, at least two ports opening into said interior space, and at least one pump for pumping blood between the ports through said interior space, the ports and interior space providing a continuous blood flow path that is not interrupted by valves.

3 Claims, 5 Drawing Sheets

HEART ASSIST DEVICE

CROSS-REFERENCE TO RELATED APPLICATIONS

This application is a continuation of U.S. application Ser. No. 12/934,300, filed on Dec. 2, 2010, which claims the priority of PCT/GB2008/050217, filed on Mar. 26, 2008, the entire contents of which is hereby incorporated in total by reference.

FIELD OF THE INVENTION

The present invention relates to a heart assist device and more particularly, though not necessarily, to an improved implantable left ventricular assist device.

BACKGROUND TO THE INVENTION

A ventricular assist device, or VAD, is a mechanical device used to help either one or both ventricles of the heart to pump blood. VADs are designed to assist either the right (RVAD) or left (LVAD) ventricle, or both at once (BVAD). The choice of device depends on the underlying heart condition, although LVADs are the most widely used.

In early procedures, the VAD pump was placed outside the body. More recently, the most commonly used VADs comprise an integrated pump and are implanted during open or closed-heart surgery, with a control line passing through the skin to a body worn controller. The use of implanted VADs with integrated pumps improves patient mobility and therefore a patient's capacity to lead a near normal life outside hospital.

Some VADs make use of continuous-flow impeller pumps whose only moving part is a rotor. These are relatively small, easy to insert, and are expected to be reasonably durable. They are considered capable of maintaining adequate circulation, although their capability to fully unload the ventricle is questionable. Furthermore, the use of these pumps requires full anti-coagulation therapy coupled with antiplatelet medication and there is a risk of bleeding and/or thromboembolic complications partly caused by the very small clearance of the rotor inside the device.

Other VADs make use of centrifugal pumps in which the rotor is magnetically or mechanically suspended and, therefore, does not use ball bearings. This feature, coupled with the lower number of revolutions per minute, should provide enhanced durability. However, such VADs may also present a risk of complications including thromboembolic complications.

Up until recently, the most commonly used VADs however are pulsatile devices that mimic the natural pulsing action of the heart. These pulsatile devices use positive displacement pumps with pusher plates and inflow and outflow valves. These devices are efficient at unloading the ventricle which could help recovery of the native heart while maintaining circulation. Pulsatile devices do, however, have several disadvantages, such as their large size and complexity, which can increase the risk associated with insertion, predispose the patient to infection, and compress adjacent organs. They may also contain many moving parts that can affect their durability.

FIG. 1 illustrates a pulsatile type LVAD in situ. An inflow tube 1 is inserted into the apex of the left ventricle. Upon contraction of the ventricle, blood passes through the inflow tube 1 to a pump within the device housing 2 and then out of the pump through an outflow tube 3 to the aorta. One-way valves are associated with the inflow and outflow tubes to prevent blood from flowing back from the aorta into the housing 2, or from the housing 2 to the ventricle, during the pumping action of the device. A lead 4 extends from the device, through the patient's skin, connecting the device to a power supply and to a control computer, both worn externally by the patient.

It will be appreciated that the LVAD of FIG. 1 receives a flow of blood from the left ventricle, traps this, and pushes it out to the aorta. This requires a relatively powerful pump comprising large pusher plates. This in turn requires venting of the outer sides of the pusher plates to the open air, requiring a venting tube 5 passing through the skin. Without this venting the displacement pumps would consume excessive power, as they would have to displace the pusher plates against a vacuum.

Whilst conventional LVADs can provide significant therapeutic benefits, they may also give rise to complications including infection, immunosuppression, clotting with resultant stroke, and bleeding secondary to anticoagulation. By way of example, there is a high risk of the formation of blood clots within an LVAD in regions where blood flow is stagnant and this in turn requires the use of anticoagulation therapy in order to prevent thrombosis (clotting). The use of anti-coagulants then leads to an increased risk of bleeding.

The design of existing commonly used VADs suffers from a number of other weaknesses. The implantable devices are generally large (in the region of 120 cc in volume) and heavy and usually require open-heart surgery for implantation with the associated risks. Their large size also prevents these devices from being placed within the chest cavity, due to lack of space, so that they are usually positioned in the stomach area, making it necessary to use a more powerful pump given the increased distance over which the blood is required to travel.

Evidence has shown that the use of LVADs, in conjunction with an appropriate drug therapy, can potentially lead to recovery of the patient without the need for further, more drastic treatment. It would be desirable to use LVADs in a greater number of patients. However, the risks associated with open heart surgery, as required to implant the existing LVADs, and with other complications is too great for those patients with less severe heart conditions. In addition, the size of existing devices mean that they are only suitable for use in patients weighing more than around 70 kg, preventing their use in small adults or children. A smaller and more reliable LVAD that could be implanted using less invasive techniques would likely increase the use of LVADs.

WO 2000/076288 discloses a different approach to assisting the heart and makes use of an inflatable cuff around the aorta. Inflating the cuff contracts the aorta and deflating the cuff allows the aorta to expand—in effect the aorta becomes a second left ventricle. The device described has potential advantages in avoiding the need to operate on the heart itself and in avoiding any contact between blood and the device. However this method poses a potentially significant risk of damage to the tissue of the aorta and histological changes have been observed in the outer wall of the aorta during animal and early clinical trials of such a device.

SUMMARY OF THE INVENTION

According to a first aspect of the present invention there is provided a ventricular assist device comprising a housing defining an interior space, at least two ports opening into said interior space, and at least one pump for pumping blood between the ports through said interior space, the ports and interior space providing a continuous blood flow path that is not interrupted by valves.

Embodiments of the present invention provide a failsafe mechanism providing an "open circuit" joined to the main aorta as the device does not restrict blood flow from the heart into the arterial system. They also reduce the complexity and number of components required in the device leading to a reduction in the size and cost of manufacture as well as a reduction in the number of potential points of failure.

Preferably, the housing defines a substantially cylindrical interior space. The ports can comprise a curved tube that substantially retains its shape in situ, the direction of curvature of the ports being substantially opposite and wherein said ports open into said interior space at substantially diametrically opposed, axially spaced locations and substantially tangentially to the inner surface of the housing defining the inner space. The configuration of the ports, including their curvature and different planes of entry and exit into the housing, helps achieve a smooth helical passage of blood without stasis or turbulence. In addition this helical pattern of flow blends with that in the aorta.

Embodiments of the present invention reduce the risk of some of the complications usually associated with VADs. The shape of the device ensures that blood within it "swirls" into and out of the device, allowing for a smooth continuous flow pattern and avoiding stagnant areas where clotting may occur. As a consequence, this reduces the need for anticoagulation therapy and therefore the risk of bleeding.

In a further embodiment of the invention, the device comprises a pair of pumps for pumping blood between the ports through said interior space, each pump comprising a pusher plate disposed at an end surface of the interior space with a driving device disposed between the pusher plate and an inner surface of the housing and a flexible diaphragm coupling the edge of the or each pusher plate to an interior of the housing.

Embodiments of the present invention provide for increased pumping capacity. They also provide a fail-safe in so far as should one pump fail the other can still provide assistance. In addition, a second pump could compensate for a first pump that has failed.

In a preferred embodiment of the invention the driving device can comprise a linear oscillator actuator or an electroactive polymer material.

Embodiments of the present invention using of electroactive polymer materials, avoids the requirement for separate actuator motors, further reducing size and power requirements of the device.

Preferably, the device is configured to fit within the chest cavity of a patient, adjacent to the heart with a first of said ports grafted to a posterolateral section of the ascending aorta and a second of the ports grafted to an auterolateral section of the ascending aorta or to the aortic arch.

Embodiments of the present invention enable the device to make use of the action of the aortic valve to prevent back-flow into the ventricle and removing the need for artificial valves, around which there is a significant risk of clotting as well as a problem of durability. The small amount of reverse flow that does occur is directed into the coronary arteries by the aortic valve, significantly enhancing the natural flow of blood into the coronary arteries.

Embodiments of the present invention also allow it to take full advantage of the initial momentum provided by the pumping of the heart, even if only provided by a weak heart, such that a smaller, less powerful pump can be used to achieve similar performance as the known alternatives. The reduced size of the device provides the possibility of insertion using mini-invasive endoscopic techniques, eliminating the need for heart surgery and therefore reducing the risks associated with implantation.

According to a second aspect of the present invention there is provided a ventricular assist system comprising a device according to any one of the preceding embodiments, a power supply coupled to the or each pump and a controller for synchronising the operation of the or each pump to the phases of the heart.

In a preferred embodiment of the invention, said controller causing the or each pump to counter-pulsate with respect to the left ventricle. A sensor for detecting an ECG signal of a patient can be coupled to said controller.

According to a third aspect of the present invention there is provided a method of treating a human body and comprising implanting a ventricular assist device within the chest cavity of the body, attaching a first port of the device to a posterolateral section of the ascending aorta and attaching a second port to an anterolateral section of the ascending aorta or to the aortic arch, and operating the ventricular assist device to pump blood between said first and second ports.

Preferably, the ventricular assist device is operated as a counter-pulsator, pumping blood between said ports during the ventricular diastole phase. Further, the ventricular assist device can be operated so as to pump during certain diastole phases and to rest during intervening diastole phases.

Embodiments of the present invention provide that when the device is not configured to assist the heart on every beat, but with some reduced frequency, blood will still flow through the device without the action of the pump, allowing this natural blood flow to wash out the pump volume and providing a further mechanism for reducing the risk of thrombosis.

In a preferred embodiment, said ventricular assist device being a device according to a first aspect of the invention.

DETAILED DESCRIPTION OF CERTAIN EMBODIMENTS OF THE INVENTION

Figure 1:
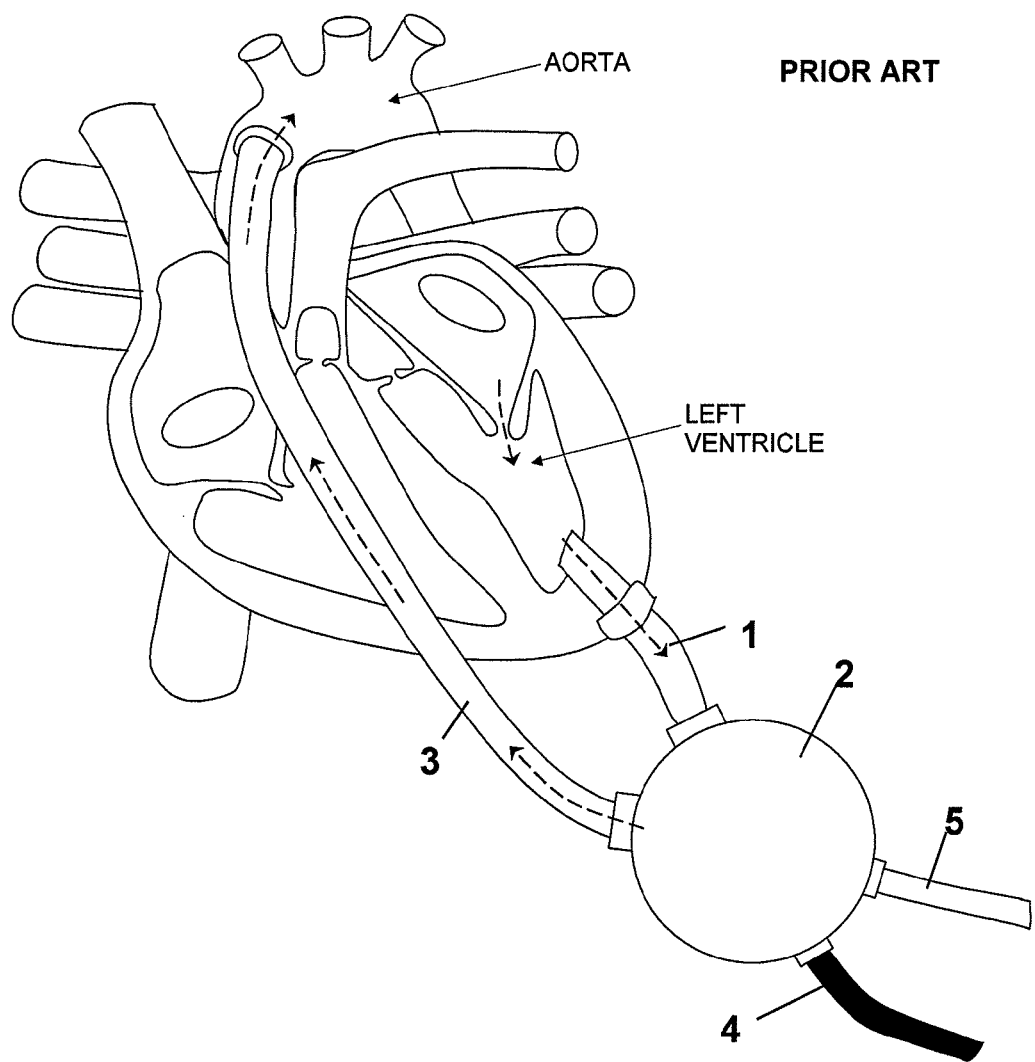
FIG. 1 illustrates a known left ventricular assist device fitted to the heart.
Figure 2:
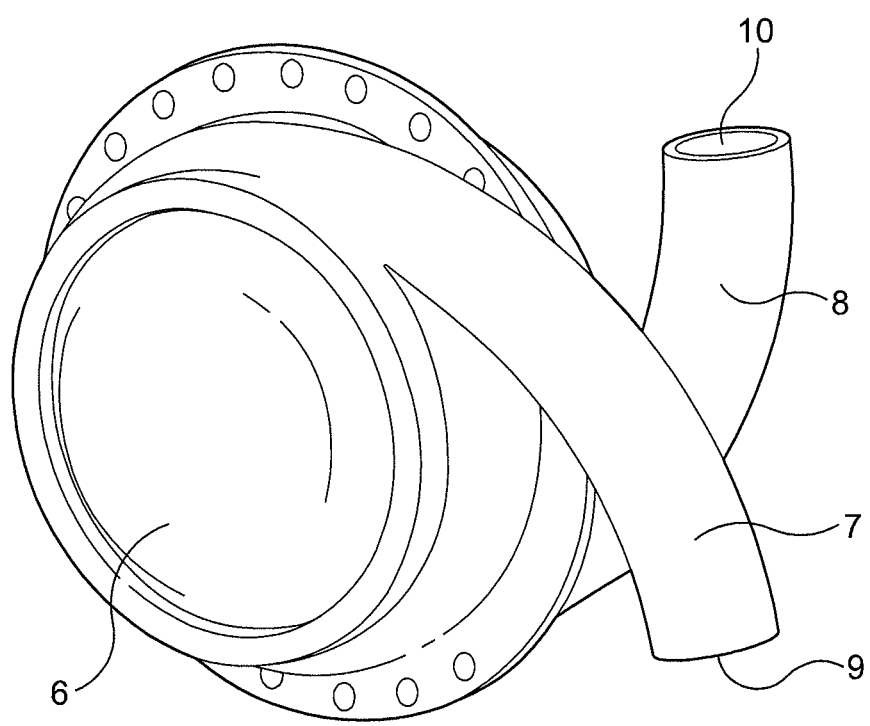
FIG. 2 is a perspective view of a left ventricular assist device according to an embodiment of the present invention.

FIG. 2 shows a LVAD comprising left and right side plates secured together with an airtight seal to form a generally hollow cylindrical housing 6. Each of the side plates is connected to or formed integrally with a curved hollow tube 7, 8. When the side plates are secured together the tubes 7, 8 open into the hollow interior of the housing at substantially diametrically opposed locations, entering the housing with a curvature that follows that of the curved interior surface of the housing. The ends of the tubes remote from the housing, referred to hereinafter as the "descending port" 9 and "ascending port" 10, face in substantially opposite directions. Neither the tubes 7,8 nor the housing 6 are provided with valves.

The side plates forming the housing, and the tubes, are made from a durable, biocompatible material such as titanium or moulded polyurethane. The hollow interior of the housing can have a volume in the region of 60 cc to 80 cc and the internal diameter of the tubes can be around 10 to 14 mm.

Figure 3:
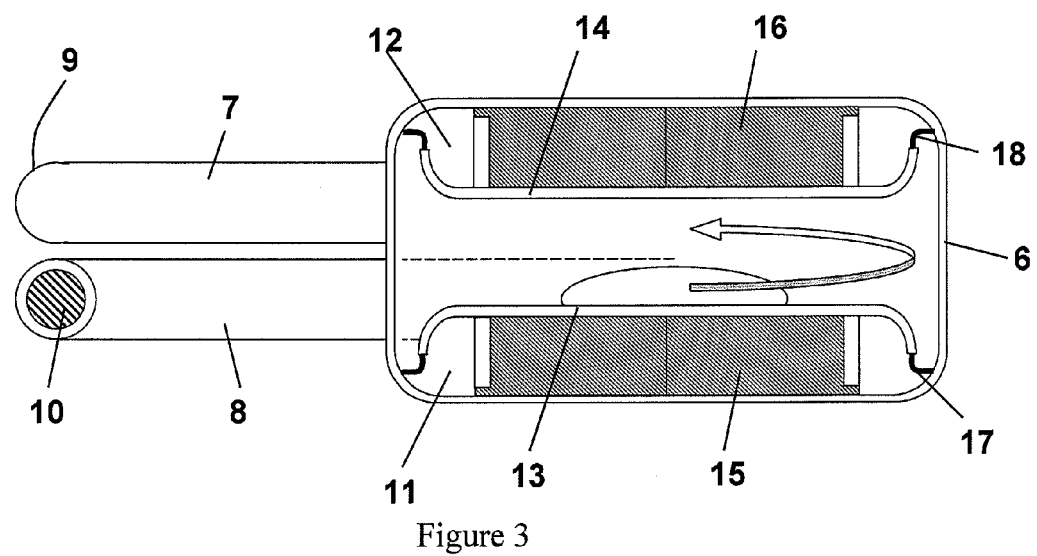
FIGS. 3 and 4 illustrates cross-sectional views of the left ventricular assist device of FIG. 2 with the device in two different operating states.
Figure 4:
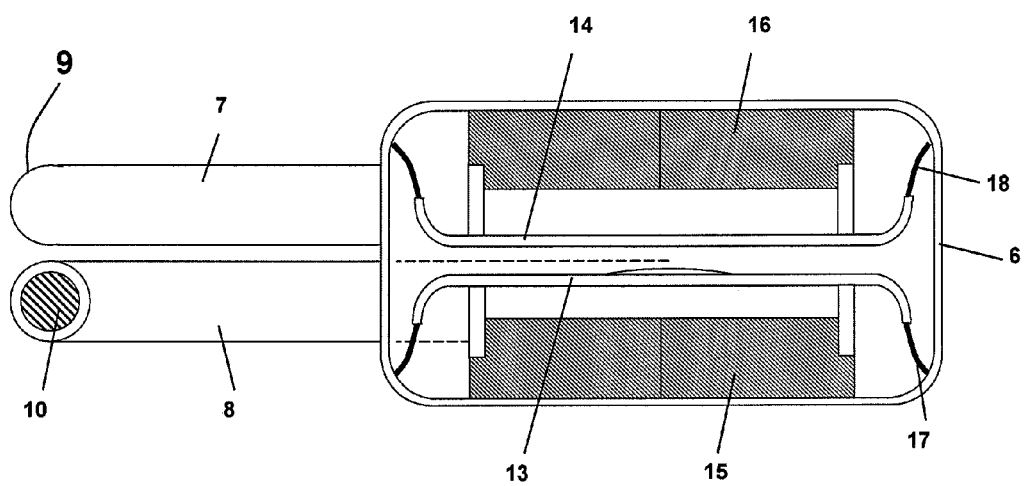

As shown in FIGS. 3 and 4, two pumps 11,12 are attached to respective inner side walls of the housing 6. Each pump comprises a generally circular pusher-plate 13,14 that is driven by a linear oscillatory actuator (LOA) 15, 16, an example of which is given in U.S. Ser. No. 10/309,045. The pusher-plates are made from a durable, biocompatible material such as titanium or moulded polyurethane. The edges of the pusher-plates are connected to the housing by a flexible annular diaphragm 17, 18 made from a durable, biocompatible material such as segmented polyurethane. When the pumps are "retracted" there is a volume available within the interior of the housing that can fill with blood (FIG. 3) whilst "activation" of the pumps drives the pusher-plates to reduce this available volume (FIG. 4). The two pumps 11,12 have an approximate combined capacity in the range of 20 cc to 50 cc and are powered and controlled by an external power source and computer as described below. The operation of the device will now be described.

Figure 5:
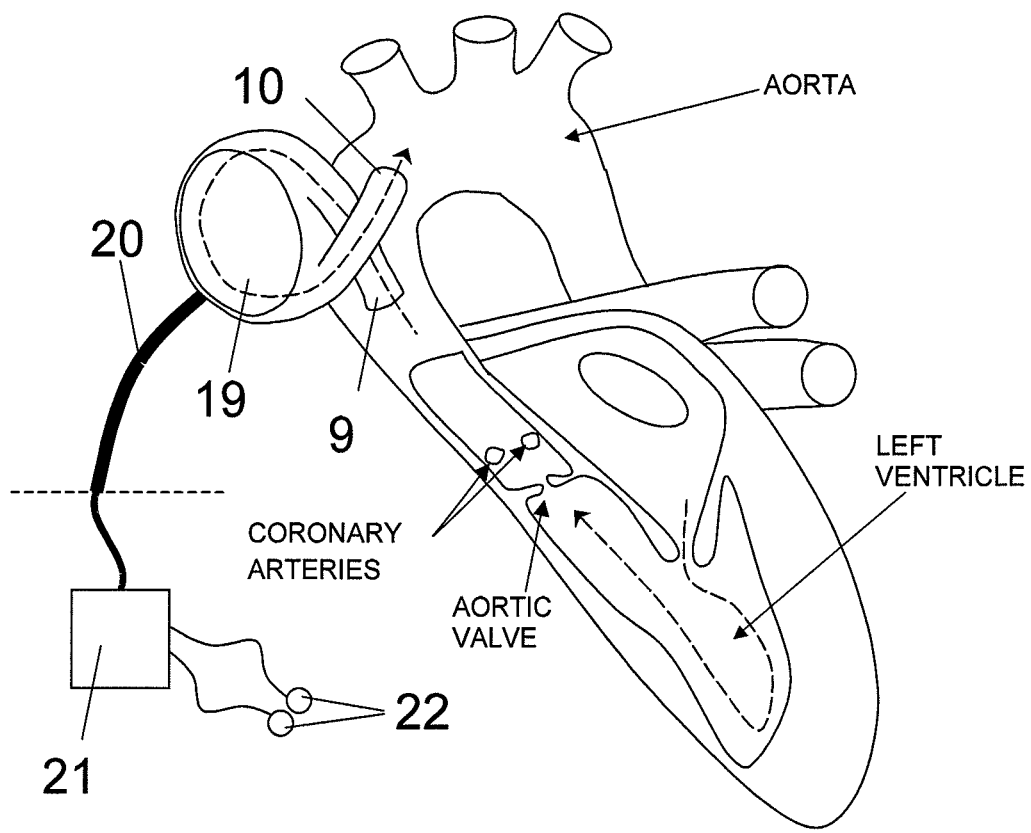
FIG. 5 is an illustration of the left ventricular assist device of FIG. 2 fitted to the left side of the heart.

FIG. 5 illustrates the device described above grafted onto the ascending aorta of the heart. The descending port 9 is grafted closest to the heart, into the posterolateral lower section of the aorta adjacent to the aortic valve, but above the coronary arteries. The ascending port 10 is grafted onto the auterolateral section on the right hand side of the aorta where it curves into the aortic arch. The location of the device and the eccentricity of the ascending and descending ports enables the flow from the device to follow and enhance the normal helical flow within the ascending aorta and provides a continuous flow pattern with no areas of stasis. A power and control line 20 extends from the device 19, through the patient's skin, connecting the device to a power supply and to a control computer 21, both worn externally by the patient. As an alternative to a percutaneous wire, and its associated infection risk, the power supply could make use of a Transcutaneous Energy Transfer System (TETS). Of course, the power supply and controller could potentially be fully integrated into the device allowing for total implantation of the system.

The control computer 21 is coupled to ECG sensors 22 and is thereby able to detect the patient's heartbeats. The control computer uses these signals to synchronise the pumps to the contraction and expansion of the left ventricle. More particularly, the control computer detects the beginning of each QRS complex (see FIG. 6) and actuates the pumps accordingly. In other embodiments, rather than detect an ECG signal, the control computer may use pressure measurements (pressure sensing devices using Surface Acoustic Wave (SAW) and Micro-Electro-Mechanical Systems (MEMS) technology are under development) or the audible sound of the heart (i.e the particular noise made by the shutting of the aortic valve) or of blood flowing in the arteries to control the pumps. Whilst FIG. 5 shows ECG sensors 22 as directly coupled to an external control computer, any sensors to be used could be implanted along with the device.

Figure 6:
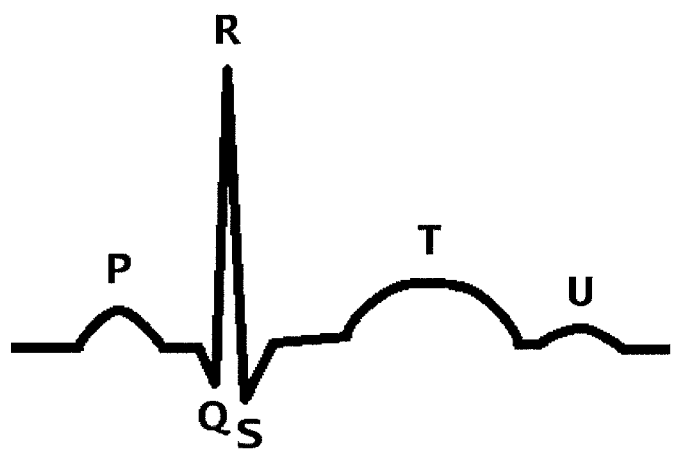
FIG. 6 illustrates the component parts of an ECG signal segment.

As shown in FIG. 6, the contraction of the left ventricle, during the ventricular systole phase, pushes blood out through the aortic valve into the aorta and into the interior volume of the device 19. The filling of the device 19 may be assisted by the active withdrawal by the linear actuators of the pusher plates 13,14 under the control of the control computer, therefore reducing the pressure and resistance to the emptying of the natural heart, or applying suction, within the housing 6 and thus reducing any resistance to filling that may occur. The aortic valve then shuts and the heart enters the ventricular diastole phase.

Figure 7:
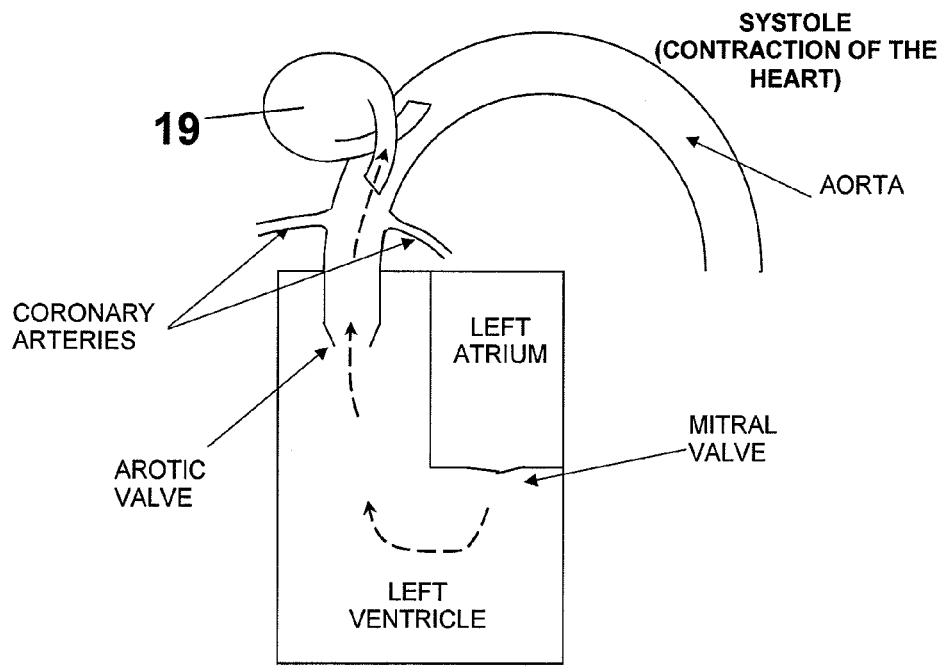
FIGS. 7 and 8 are simplified illustrations of the left ventricular assist device of FIG. 2 fitted to the left side of the heart.
Figure 8:
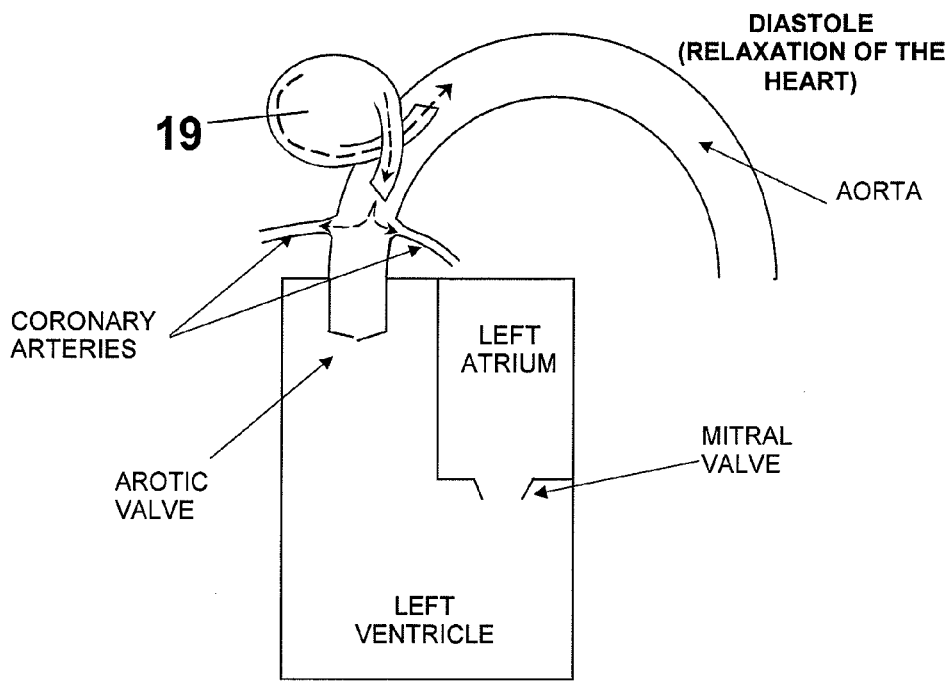

At this point the control computer causes the linear actuators to drive the pusher-plates 13,14 into the interior of the housing 6, reducing the available volume and forcing blood out through the tubes 7,8 and out of the ports 9,10. Due to the shape of the device 19 the blood flow within the housing 6 follows a generally helical path, with the initial momentum of the blood within the device 19 being provided by the pumping action of the heart. The action of the pusher plates 13,14 causes the majority of blood within the device to follow this helical path out of the device 19, away from the heart and through the ascending port 10. A small volume of blood will also flow in the reverse direction i.e. out through the descending port 9, back towards the heart (FIG. 7). As the aortic valve is shut during ventricular diastole, this reverse flow is directed into the coronary arteries resulting in an increased flow through the arteries and enhanced perfusion of the muscle tissue of the heart.

In effect, the device provides a second beat during the ventricular diastole phase that assists the blood flow in the arterial system: it can be described as a counter pulsating device, pulsing out of phase with the beat of the heart. The cycle is repeated at a frequency dependent upon the patient's requirements, i.e. the cycle can repeat each time the heart beats or on every second or third beat. The amount of assist or volume of blood pumped by the device can be varied.

The control computer 21 worn externally by the patient controls aspects of the pumping action of the device as has been described. In addition, the control computer can potentially make use of sensors disposed within the device to measure the rates of blood flow into and out of the device in order to adapt the device performance to that of the heart.

The device described reduces the risk of some of the complications usually associated with LVADs. The shape of the device ensures that blood within it "swirls" into and out of the device, allowing for a smooth continuous flow pattern and avoiding stagnant areas where clotting may occur. As a consequence, this reduces the need for anticoagulation therapy and therefore the risk of bleeding.

A number of advantages arise as both the ascending and descending ports of the device are grafted into the ascending aorta of the heart. This enables the device to make use of the action of the aortic valve to prevent back-flow into the ventricle and removing the need for artificial valves, around which there is a significant risk of clotting.

The valve-less mechanism is essentially a failsafe mechanism providing an "open circuit" joined to the main aorta. If there is a fault with the device, e.g. a power or sensor failure, the device does not restrict blood flow from the heart into the arterial system. The valve-less mechanism also reduces the complexity and number of components required in the device leading to a reduction in the size and cost of manufacture as well as a reduction in the number of potential points of failure. The valve-less design and the intended location of the device also significantly enhance the natural flow of blood into the coronary arteries, as a result of the small amount of reverse flow that occurs.

In addition, it is recognised that conventional LVADs fail to make efficient use of the initial momentum of the blood provided by the pumping of the heart and therefore require larger, more powerful pumps to ensure that the required degree of assistance is achieved. The shape, valve-less design and implanted location of the LVAD described here allows it to take full advantage of this initial momentum, even if only provided by a weak heart, such that a smaller, less powerful pump can be used to achieve a similar performance to the known alternatives. The reduced size of the device provides the possibility of insertion using mini-invasive endoscopic techniques, eliminating the need for open-heart surgery and therefore reducing the risks associated with implantation.

A still further advantage arises when the device is not configured to assist the heart on every beat, but with some reduced frequency. During a "resting" cycle, where the device is not activated, blood will still flow through the device without the action of the pump, allowing this natural blood flow to wash out the pump volume and providing a further mechanism for reducing the risk of thrombosis.

The use of dual-pumps provides a further fail-safe in so far as should one pump fail the other can still provide assistance. In addition, the control computer could be programmed to enhance the action of the functioning pump, i.e. increasing the frequency at which the pump is activated, to compensate for the pump which has failed. When functioning normally of course dual pumps provide for increased pumping capacity.

These advantages mean that the device described above could be used in a greater number of patients than existing devices, such as children and small adults, as well as those patients with less severe heart conditions. The device can act as a 'bridge to recovery', providing sufficient support to the heart to potentially allow it to recover, without incurring the same level of risk as incurred by existing device.

As an alternative to the use of pusher-plates driven by linear actuators or other mechanisms, the pump can make use of pusher-plates made of an artificial muscle material that is driven by electrical stimulation. An example of an electroactive polymer actuator for use as a small-sized diaphragm pump is given in EP1323925. The use of electroactive polymer materials (EPAM) that respond to electrical stimulation by displaying a significant shape or size displacement, avoids the requirement for separate actuator motors, reducing size and power requirements of the device still further.

It will be appreciated by those of skill in the art that various modifications may be made to the above described embodiments without departing from the scope of the present invention.

The invention claimed is:

1. A method of treating a human body, comprising implanting a ventricular assist device within the chest cavity of the body, attaching a first port of the device to a posterolateral section of the ascending aorta and attaching a second port to an anterolateral section of the ascending aorta or to an anterolateral section of the aortic arch, and operating the ventricular assist device to pump blood between said first and second ports.

2. A method according to claim 1, further comprising operating the ventricular assist device as a counter-pulsator, pumping blood between said ports during the ventricular diastole phase.

3. A method according to claim 2, further comprising operating the ventricular assist device to pump during certain diastole phases and to rest during intervening diastole phases.

* * * * *